US012788728B2

(12) United States Patent
Gelfand et al.

(10) Patent No.: US 12,788,728 B2
(45) Date of Patent: Nov. 10, 2026

(54) COMPOSITIONS OF VITAMIN A PALMITATE, PROCESSES FOR THEIR PREPARATION, USES AND METHODS COMPRISING THEM

(71) Applicant: Advent Therapeutics Inc., Lumberville, PA (US)

(72) Inventors: Craig Gelfand, Jackson, NJ (US); Robert Segal, Gwynedd Valley, PA (US); David Lopez, Lumberville, PA (US)

(73) Assignee: Advent Therapeutics, Inc., Lumberville, PA (US)

( * ) Notice: Subject to any disclaimer, the term of this patent is extended or adjusted under 35 U.S.C. 154(b) by 1036 days.

(21) Appl. No.: 17/798,874

(22) PCT Filed: Jan. 31, 2021

(86) PCT No.: PCT/US2021/015958

§ 371 (c)(1),
(2) Date: Aug. 10, 2022

(87) PCT Pub. No.: WO2021/162880

PCT Pub. Date: Aug. 19, 2021

(65) Prior Publication Data

US 2023/0106684 A1 Apr. 6, 2023

Related U.S. Application Data

(60) Provisional application No. 62/972,784, filed on Feb. 11, 2020.

(51) Int. Cl.

| | |
|---|---|
| ***A61K 31/07*** | (2006.01) |
| ***A61K 9/107*** | (2006.01) |
| ***A61K 31/20*** | (2006.01) |
| ***A61K 47/10*** | (2017.01) |
| ***A61K 47/26*** | (2006.01) |
| ***A61K 47/60*** | (2017.01) |

(52) U.S. Cl.

CPC .............. *A61K 31/07* (2013.01); *A61K 9/107* (2013.01); *A61K 31/20* (2013.01); *A61K 47/10* (2013.01); *A61K 47/26* (2013.01); *A61K 47/60* (2017.08)

(58) Field of Classification Search

CPC ...... A61K 9/1075; A61K 31/07; A61K 31/20; A61K 9/107

See application file for complete search history.

(56) References Cited

U.S. PATENT DOCUMENTS

| | | | |
|---|---|---|---|
| 3,826,255 | A | 7/1974 | Havstad et al. |
| 4,046,146 | A | 9/1977 | Rosskamp et al. |
| 4,253,468 | A | 3/1981 | Lehmbeck |
| 4,263,907 | A | 4/1981 | Lindsey |
| 4,268,460 | A | 5/1981 | Boiarski et al. |
| 4,510,929 | A | 4/1985 | Bordoni et al. |
| 4,624,251 | A | 11/1986 | Miller |
| 4,649,911 | A | 3/1987 | Knight et al. |
| 5,112,598 | A | 5/1992 | Biesalski |
| 5,164,740 | A | 11/1992 | Ivri |
| 5,411,988 | A | 5/1995 | Bockow et al. |
| 5,549,102 | A | 8/1996 | Lintl et al. |
| 5,586,550 | A | 12/1996 | Ivri et al. |
| 5,603,314 | A | 2/1997 | Bono |
| 5,611,332 | A | 3/1997 | Bono |
| 5,630,409 | A | 5/1997 | Bono et al. |
| 5,709,202 | A | 1/1998 | Lloyd et al. |
| 5,758,637 | A | 6/1998 | Ivri et al. |
| 5,823,179 | A | 10/1998 | Grychowski et al. |
| 5,906,202 | A | 5/1999 | Schuster et al. |
| 5,934,272 | A | 8/1999 | Lloyd et al. |
| 5,960,792 | A | 10/1999 | Lloyd et al. |
| 5,971,951 | A | 10/1999 | Ruskewicz |
| 6,070,575 | A | 6/2000 | Gonda et al. |
| 6,083,922 | A | 7/2000 | Montgomery |
| 6,161,536 | A | 12/2000 | Redmon et al. |
| 6,192,876 | B1 | 2/2001 | Denyer et al. |
| 6,196,219 | B1 | 3/2001 | Hess et al. |
| 6,230,703 | B1 | 5/2001 | Bono |
| 6,230,706 | B1 | 5/2001 | Gonda et al. |
| 6,264,922 | B1 | 7/2001 | Wood et al. |
| 6,338,443 | B1 | 1/2002 | Piper |
| 6,349,719 | B2 | 2/2002 | Gonda |

(Continued)

FOREIGN PATENT DOCUMENTS

| | | | |
|---|---|---|---|
| AU | 6985691 A * | 7/1991 | ........... A61K 9/1075 |
| CA | 2748788 A1 * | 7/2010 | .............. A61P 31/16 |

(Continued)

OTHER PUBLICATIONS

Counts et al, The effect of retinyl palmitate on skin composition and morphometry, J.Soc.Cosmet.Chem., 39, 235-240, Jul./Aug. 1988 (Year: 1988).*

Mitra et al., "Chapter 7: Nanoscale drug delivery systems; 7.5 Micelles", Advanced Drug Delivery, 2013, pp. 1-4.

Huang et al., "Chapter 7 Formulations Strategies and Practice Used for Drug Candidates with Water-Insoluble Properties for Toxicology, Biology, and Pharmacology Studies in Discovery Support", Water-Insoluble Drug Formulation, 2008, pp. 119-120.

(Continued)

*Primary Examiner* — Bethany P Barham

*Assistant Examiner* — Danielle Johnson

(74) *Attorney, Agent, or Firm* — Armstrong Teasdale LLP

(57) ABSTRACT

The present invention provides pharmaceutical compositions comprising a therapeutically effective dose of vitamin A palmitate; processes for their preparation, and uses and methods of treatment comprising them. The compositions provided by the present invention may be used in the treatment and/or prophylaxis of conditions and diseases caused by vitamin A deficiency.

16 Claims, No Drawings

(56) References Cited

U.S. PATENT DOCUMENTS

| | | | |
|---|---|---|---|
| 6,367,470 | B1 | 4/2002 | Denyer et al. |
| 6,543,442 | B2 | 4/2003 | Gonda et al. |
| 6,557,549 | B2 | 5/2003 | Schmidt et al. |
| 6,584,971 | B1 | 7/2003 | Denyer et al. |
| 6,601,581 | B1 | 8/2003 | Babaev |
| 6,612,303 | B1 | 9/2003 | Grychowski et al. |
| 6,644,304 | B2 | 11/2003 | Grychowski et al. |
| 7,476,380 | B2 | 1/2009 | Frankenberger et al. |
| 8,026,276 | B2 | 9/2011 | Rubino et al. |
| 2003/0190347 | A1 | 10/2003 | Supersaxo et al. |
| 2005/0238675 | A1 | 10/2005 | Li et al. |

FOREIGN PATENT DOCUMENTS

| | | | | | |
|---|---|---|---|---|---|
| CN | 109187829 | B | * | 7/2021 | ............ G01N 30/06 |
| DE | 202004003241 | U1 | | 7/2005 | |
| EP | 0165352 | A2 | | 12/1985 | |
| GB | 996207 | | | 6/1965 | |
| JP | 11-236331 | A | | 8/1999 | |
| JP | 11-302195 | A | | 11/1999 | |
| JP | 11-335266 | A | | 12/1999 | |
| JP | 2013-253063 | A | | 12/2013 | |
| WO | 2006079209 | | | 8/2006 | |
| WO | 2016/004369 | | | 1/2016 | |
| WO | 2016188876 | | | 12/2016 | |
| WO | 2018045174 | | | 3/2018 | |

OTHER PUBLICATIONS

Boylan et al., "D. Parenteral Products", Modern Pharmaceutics, 2002, pp. 594.
Pamudji et al, "Development of Nanostructured Lipid Carrier Formulation Containing of Retinyl Palmitate," International Journal of Pharmacy and Pharmaceutical Sciences, vol. 8, Issue 2, pp. 256-260 (2016).
Office Action dated Jul. 30, 2024 received from the Japanese Patent Office for Japanese Patent Application No. 2022-574339.
Kriegel et al., "Pediatric Safety of Polysorbates in Drug Formulations", Children, 2020, 7, pp. 1-12.
Dizaj, "Preparation and study of vitamin A palmitate microemulsion drug delivery system and investigation of co-surfactant effect", Journal of Nanostructure in Chemistry, 2013, 3(59), pp. 1-6.
Search Report (noted as completed May 27, 2024) and Written Opinion (dated May 28, 2024) received from the International Property Office of Singapore for Singaporean Patent Application No. 11202251976P.
Anand et al., "Synergistic action of vitamin D and retinoic acid restricts invasion of macrophages by pathogenic mycobacteria", J Microbiol Immunol Infect, 2008, 41, pp. 17-25.
Anonymous, "Handbook of Pharmaceutical Manufacturing Formulations, Third Edition, vol. Three, Liquid Products", 2019, CRC Press, pp. 384-385.
Anonymous, "McFarland Standard", Dalynn Biologicals, Catalogue No. TM50-TM60, 2014, pp. 1-2.
Anonymous, "McFarland standards", Wikipedia, 2022, pp. 1-2.
Aquasol A—vitamin a palmitate injection, solution, Casper Pharma LLC Prescribing Information, 2019, pp. 1-6.
Baker et al., "Disrupted lung development and bronchopulmonary dysplasia: opportunities for lung repair and regeneration", Curr Opin Pediatr, 2014, 26(3), pp. 306-314.
Baybutt et al., "Vitamin A deficiency injures lung and liver parenchyma and impairs function of rat type II pneumocytes", J Nutr, 2000, 130(5), pp. 1159-1165.
Beasley et al., "Preservatives in nebulizer solutions: risks without benefit," Pharmacotherapy, 1998, 18(1), pp. 130-139.
Bhandari et al., "BPD Following Preterm Birth: A Model for Chronic Lung Disease and a Substrate for ARDS in Childhood", Front Pediatr, 2016, 4(60), pp. 1-7.
Biesalski et al., "Retinyl palmitate supplementation by inhalation of an aerosol improves vitamin A status of preschool children in Gondar (Ethiopia)", Br J Nutr, 1999, 82(3), pp. 179-182.
Borody et al., "Chlorbutanol toxicity and dependence", Med J Aust, 1979, 1, pp. 288.
Campbell, "Intensive oxygen therapy as a possible cause of retrolental fibroplasia; a clinical approach", The Medical Journal of Australia, 1951, 2(2), pp. 48-50.
Cerny et al., "Prevention and treatment of bronchopulmonary dysplasia: contemporary status and future outlook", Lung, 2008, 186(2), pp. 75-89.
Chisholm et al., "Fluorescent Retinoic Acid Analogues as Probes for Biochemical and Intracellular Characterization of Retinoid Signaling Pathways", ACS Chem Biol, 2019, 14(3), pp. 369-377.
Christie et al., "Synthesis and evaluation of synthetic retinoid derivatives as inducers of stem cell differentiation", Organic & Biomolecular Chemistry, 2008, 6, pp. 3497-3507.
Chytil, "The lungs and vitamin A", Am J Physiol, 1992, 262(5 Pt 1), pp. L517-L527.
Coleman et al., "All-trans Retinoic Acid Augments Autophagy during Intracellular Bacterial Infection", American J of Respir Cell and Mol Biol, 2018, 59(5), pp. 548-556.
Couroucli et al., "Should we still use vitamin A to prevent bronchopulmonary dysplasia?", J Perinatol, 2016, 36(8), pp. 581-585.
Da Silva et al., "Plasma vitamin A levels in deprived children with pneumonia during the acute phase and after recovery", J Pediatr (Rio J), 2005, 81(2), pp. 162-168.
Daniels et al., "Nasal Sinusitis Produced By Diets Deficient In Fat-Soluble A Vitamin", JAMA, 1923, 81(10), pp. 828-829.
Darlow et al., "Vitamin A supplementation to prevent mortality and short- and long-term morbidity in very low birth weight infants", Cochrane Database of Systematic Reviews, 2016, 8, pp. 1-60.
Dasgupta et al., "Hyperoxia-induced neonatal rat lung injury involves activation of TGF-beta and Wnt signaling and is protected by rosiglitazone", Am J Physiol Lung Cell Mol Physiol, 2009, 296(6), pp. L1031-L1041.
Dechristoforo et al., "High-dose morphine infusion complicated by chlorobutanol-induced somnolence", Annals of Internal Medicine, 1983, 98, pp. 335-336.
Dias-Freitas et al., "Molecular mechanisms underlying hyperoxia acute lung injury", Respir Med, 2016, 119, pp. 23-28.
Dux et al., "Hypersensitivity reaction to chlorbutanol-preserved heparin", Lancet, 1981, 1, pp. 149.
Ehrenkranz et al., "Validation of the National Institutes of Health Consensus Definition of Bronchopulmonary Dysplasia", Pediatrics, 2005, 116(6), pp. 1353-1360.
European Pharmacopeia 7.0, "2.2.1 Clarity and degree of opalescence of liquids", 2008, pp. 21-22.
Fauvart et al., "Stabbed while Sleeping: Synthetic Retinoid Antibiotics Kill Bacterial Persister Cells", 2018, 70(5), pp. 763-764.
Gelfand et al., "Inhaled vitamin A is more effective than intramuscular dosing in mitigating hyperoxia-induced lung injury in a neonatal rat model of bronchopulmonary dysplasia", Am J Physiol Lung Cell Mol Physiol, 2020, 319, pp. L576-L584.
Green et al., "It's agony for US as well: Neonatal nurses reflect on iatrogenic pain", Nurs Ethics, 2016, 23(2), pp. 176-190.
Greene et al., "Persistently low blood retinol levels during and after parenteral feeding of very low birth weight infants: examination of losses into intravenous administration sets and a method of prevention by addition to a lipid emulsion", Pediatrics, 1987, 79(6), 894-900.
Greenough et al., "Lung vols. in infants who had mild to moderate bronchopulmonary dysplasia", Eur J Pediatr, 2005, 164(9). pp. 583-586.
Guimaraes et al., "Vitamin A in prevention of bronchopulmonary dysplasia", Curr Pharm Des, 2012, 18(21), pp. 3101-3113.
Hind et al., "Retinoic acid induces alveolar regeneration in the adult mouse lung", Eur Respir J, 2004, 23(1), pp. 20-27.
Huang et al., "Role of Vitamin A in the Immune System", J Clin Med, 2018, 7(258), pp. 1-16.
Hustead et al., "Relationship of vitamin A (retinol) status to lung disease in the preterm infant", J Pediatr, 1984, 105 (4), pp. 610-615.
Ibrahim et al., "Wound Healing Properties of Selected Natural Products", Int J Environ Res Public Health, 2018, 15 (2360), pp. 1-23.

(56) References Cited

OTHER PUBLICATIONS

International Search Report and Written Opinion mailed Apr. 23, 2021 by the European Patent Office for international patent application No. PCT/US2021/015958.
International Search Report and Written Opinion mailed Sep. 17, 2021 by the European Patent Office for International patent application No. PCT/US2021/035210.
Iyer et al., "Vitamin A at the interface of host-commensal-pathogen interactions", PLoS Pathog, 2019, 15(6), pp. e1007750.
Janssen et al., "Vitamin K metabolism as the potential missing link between lung damage and thromboembolism in Coronavirus disease 2019", Br J Nutr, 2021, 126(2), pp. 191-198.
Japanese Pharmacopeia, "General Test, Processes and Apparatus", 2016, pp. 25-358.
Jee et al., "Effects of dietary vitamin A content on antibody responses of feedlot calves inoculated intramuscularly with an inactivated bovine coronavirus vaccine", Am J Vet Res, 2013, pp. 1353-1362.
Kalmar et al., "Primary structure and expression of a human CTP:phosphocholine cytidylyltransferase", Biochim Biophys Acta, 1994, 1219, pp. 328-334.
Kennedy et al., "Prevention and management of bronchopulmonary dysplasia: Lessons learned from the neonatal research network", Seminars in Perinatology, 2016, 40(6), pp. 348-355.
Kim et al., "A new class of synthetic retinoid antibiotics effective against bacterial persisters", Nature, 2018, 556, pp. 103-107.
Lancillotti et al., "Retinoid status and the control of keratin expression and adhesion during the histogenesis of squamous metaplasia of tracheal epithelium", Cancer Res, 1992, 52(22), pp. 6144-6152.
Levy et al., "Right ventricular function in preterm and term neonates: reference values for right ventricle areas and fractional area of change", J Am Soc Echocardiogr, 2015, 28(5), pp. 559-569.
Li et al., "Activation of Src-dependent Smad3 signaling mediates the neutrophilic inflammation and oxidative stress in hyperoxia-augmented ventilator-induced lung injury", Respir Res, 2015, 16(112), pp. 1-14.
Mactier et al., "Vitamin A and preterm infants: what we know, what we don't know, and what we need to know", Archives of Disease in Childhood Fetal and Neonatal Edition, 2005, 90(2), pp. F103-F108.
Young, "Nutritional support and bronchopulmonary dysplasia", Journal of Perinatology, 2007, 27, pp. S75-S78.
Yue et al "TGF-β: Titan of Lung Fibrogenesis", Curr Enzym Inhib, 2010, 6(2), pp. 1-20.
Yurt et al., "Vitamin D supplementation blocks pulmonary structural and functional changes in a rat model of perinatal vitamin D deficiency", Am J Physiol Lung Cell Mol Physiol, 2014, 307(11), pp. L859-L867.
Zachman et al., "Use of the intramuscular relative-dose-response test to predict bronchopulmonary dysplasia in premature infants", Am J Clin Nutr, 1996, 63(1), pp. 123-129.
Hang et al., "Low-dose vitamin A therapy on T lymphocyte function in neonatal pneumonia", Eur Rev Med Pharmacol Sci, 2018, 22(13), pp. 4371-4374.
Zhang et al., "Potential interventions for novel coronavirus in China: A systematic review", J Med Virol, 2020, 92(5), pp. 479-490.
McGill et al., "Vitamin A deficiency impairs the immune response to intranasal vaccination and RSV infection in neonatal calves", Sci Rep, 2019, 9(15157), pp. 1-14.
Mitchell et al., "Particle Size Analysis of Aerosols from Medicinal Inhalers", KONA Powder and Particle Journal, 2004, 22, pp. 32-65.
Morales et al., "Nebulized PPARgamma Agonists: A Novel Approach to Augment Neonatal Lung Maturation and Injury Repair", Pediatr Res, 2014, 75, pp. 631-640.
Morgan et al., "Radiation and the lung: a reevaluation of the mechanisms mediating pulmonary injury", Int J Radiat Oncol Biol Phys, 1995, 31(2), pp. 361-369.
Movsas et al., "Pulmonary radiation injury", Chest, 1997, 111(4), pp. 1061-1076.
Nacul et al., "Randomised, double blind, placebo controlled clinical trial of efficacy of vitamin A treatment in non-measles childhood pneumonia", BMJ, 1997, 315(7107), pp. 505-510.
National Heart, Lung and Blood Institute (NHLBI), "Bronchopulmonary Dysplasia", 2019, https://www,nhlbi.nih.gov/health-topics/bronchopulmonary-dylplasia.
NeoVitA clinical trial, 2013, EudraCT No. 2013-001998-24, https://www.clinicaltrialsregister.eu/ctr-search/search?query=2013-001998-24.
O'Reilly et al., "Impact of preterm birth and bronchopulmonary dysplasia on the developing lung: long-term consequences for respiratory health", Clin Exp Pharmacol Physiol, 2013, 40(11), pp. 765-773.
Ocallaghan et al., "The science of nebulised drug delivery", Thorax, 1997, 52(Suppl 2), pp. S31-S44.
Penkert et al., "Influences of Vitamin A on Vaccine Immunogenicity and Efficacy", Front Immunol, 2019, 10(1576), pp. 1-9.
Penkert et al., "Vitamin A deficient mice exhibit increased viral antigens and enhanced cytokine/chemokine production in nasal tissues following respiratory virus infection despite the presence of FoxP3+ T cells", Int Immunol, 2016, 28(3), pp. 139-152.
Pertzborn et al., "Continuous Albuterol With Benzalkonium in Children Hospitalized With Severe Asthma", Pediatrics, 2020, 145(4), pp. e20190107.
Preziosi et al., "Phase Inversion Emulsification", Chemical Engineering Transactions, 2013, 32, pp. 1585-1590.
Quiles et al., "Vitamin A Deficiency and the Lung Microbiome", D70 Revisiting Lung Infection and Inflammatory Axes, Am J Respir Crit Care Med, 2020, 201:A7442.
Raleigh et al., "Pulmonary availability of isotretinoin in rats after inhalation of a powder aerosol", Br J Cancer, 2000, 83(7), pp. 935-940.
Rau, "Design principles of liquid nebulization devices currently in use", Respir Care, 2002, 47, pp. 1257-1278.
Redlich et al., "Vitamin A inhibits radiation-induced pneumonitis in rats", J Nutr, 1998, 128(10), pp. 1661-1664.
Rehan et al., "In utero nicotine exposure alters fetal rat lung alveolar type II cell proliferation, differentiation, and metabolism", Am J Physiol Lung Cell Mol Physiol, 2007, 292(1), pp. L323-L333.
Rehan et al., "Perinatal nicotine-induced transgenerational asthma", Am J Physiol Lung Cell Mol Physiol, 2013, 305 (7), pp. L501-L507.
Restori et al., "*Streptococcus pneumoniae*-Induced Pneumonia and Citrobacter rodentium-Induced Gut Infection Differentially Alter Vitamin A Concentrations in the Lung and Liver of Mice", J Nutr, 2014, 144(3), pp. 392-398.
Richter et al., "Functional assessment of hyperoxia-induced lung injury after preterm birth in the rabbit", Am J Physiol Lung Cell Mol Physiol, 2014, 306(3), pp. L277-L283.
Ross et al., "The Components of VARA, a Nutrient-Metabolite Combination of Vitamin A and Retinoic Acid, Act Efficiently Together and Separately to Increase Retinyl Esters in the Lungs of Neonatal Rats", J Nutr, 2006, 136(11), pp. 2803-2807.
Rush et al., "Intramuscular versus enteral vitamin A supplementation in very low birth weight neonates", The Journal of Pediatrics, 1994, 125(3), pp. 458-462.
Sakurai et al., "Curcumin protects the developing lung against long-term hyperoxic injury", Am J Physiol Lung Cell Mol Physiol, 2013, 305(4), pp. L301-L311.
Sakurai et al., "Perinatal nicotine exposure induces myogenic differentiation, but not epithelial-mesenchymal transition in rat offspring lung", Pediatr Pulmonol, 2016, 51(11), pp. 1142-1150.
Shenai et al., "Plasma retinol-binding protein response to vitamin A administration in infants susceptible to bronchopulmonary dysplasia", J Pediatr, 1990, 116(4), pp. 607-614.
Shenai et al., "Vitamin A status and airway infection in mechanically ventilated very-low-birth-weight neonates", Pediatr Pulmonol, 1995, 19(5), pp. 256-261.
Shenai et al., "Vitamin A status of neonates with bronchopulmonary dysplasia", Pediatr Res, 1985, 19(2), pp. 185-188.
Shenai, "Vitamin A supplementation in very low birth weight neonate: rationale and evidence", Pediatrics, 1999, 104 (6), pp. 1369-1374.

(56) References Cited

OTHER PUBLICATIONS

Stoll et al., “Trends in Care Practices, Morbidity, and Mortality of Extreme Preterm Neonates”, JAMA, 2015, 314(10), pp. 1039-1051.
Strueby et al., “Advances in bronchopulmonary dysplasia”, Expert Rev Respir Med, 2014, 8(3), pp. 327-338.
Surman et al., “Vitamin Supplementation at the Time of Immunization with a Cold-Adapted Influenza Virus Vaccine Corrects Poor Mucosal Antibody Responses in Mice Deficient for Vitamins A and D”, Clin Vaccine Immunol, 2016, 23 (3), pp. 219-227.
Tan et al., “Inhibition of SARS Coronavirus Infection In Vitro with Clinically Approved Antiviral Drugs”, Emerg Infect Dis, 2004, 10(4), pp. 581-586.
Taylor et al., “Inhaled Vitamin D: A Novel Strategy to Enhance Neonatal Lung Maturation”, Lung, 2016, 194(6), pp. 931-943.
The United States Pharmacopeial Convention, “Polysorbate 80” monograph, 2017, available at https://www.usp.org/sites/default/files/usp/document/harmonization/excipients/polysorbate_80.pdf.
Tian et al., “Vitamin A supplement after neonatal *Streptococcus pneumoniae* pneumonia inhibits the progression of experimental asthma by altering CD4+T cell subsets”, Sci Rep, 2020, 10(4214), pp. 1-10.
Tin et al., “Optimum oxygen therapy in preterm babies”, Arch Dis Child Fetal Neonatal Ed, 2007, 92(2), pp. F143-F147.
Tolman et al., “Advances in the pulmonary delivery of poorly water-soluble drugs: influence of solubilization on pharmacokinetic properties”, Drug development and industrial pharmacy, 2010, 36(1), pp. 1-30.
Tropea et al., “Current pharmacologic approaches for prevention and treatment of bronchopulmonary dysplasia”, Int J Pediatr, 2012, pp. 598-606.
Tsoutsou et al., “Radiation pneumonitis and fibrosis: mechanisms underlying its pathogenesis and implications for future research”, Int J Radiat Oncol Biol Phys, 2006, 66(5), pp. 1281-1293.
Tyson et al., “Vitamin A Supplementation for Extremely-Low-Birth-Weight Infants”, New England Journal of Medicine, 1999, 340(25), pp. 1962-1968.
US Pharmacopeia General Chapters: “<1196> Pharmacopeial Harmonization”, 2002, pp. 1-10.
US Pharmacopeial Convention in Process Revision Physical Tests and Determinations “<601> Aerosols, Nasal Sprays, Metered-Dose Inhalers, and Dry Powder Inhalers”, 2012, pp. 232-253.
Van De Pavert et al., “Maternal retinoids control type 3 innate lymphoid cells and set the offspring immunity”, Nature, 2014, 508, pp. 123-127.
Werkman, “Immunologic Significance of Vitamins: II. Influence of Lack of Vitamins on Resistance of Rat, Rabbit and Pigeon to Bacterial Infection”, The Journal of Infectious Diseases, 1923, 32(4), pp. 255-262.
West et al., “Epithelia-damaging virus infections affect vitamin A status in chickens”, J Nutr, 1992, pp. 333-339.
Wiseman et al., “The vicious cycle of vitamin A deficiency: A review”, Crit Rev Food Sci Nutr, 2017, 57(17), pp. 3703-3714.
Wong et al., “Emphysema in young adult survivors of moderate-to-severe bronchopulmonary dysplasia”, Eur Respir J, 2008, 32(2), pp. 321-328.
Xing et al., “Vitamin A deficiency is associated with severe Mycoplasma pneumoniae pneumonia in children”, Ann Transl Med, 2020, 8(4), pp. 1-7.

* cited by examiner

COMPOSITIONS OF VITAMIN A PALMITATE, PROCESSES FOR THEIR PREPARATION, USES AND METHODS COMPRISING THEM

The present application is the § 371 national stage of PCT International

Application No. PCT/US2021/015958, filed Jan. 31, 2021, which claims priority to U.S. Provisional Application No. 62/972,784, filed Feb. 11, 2020. The content of the latter is incorporated herein by reference.

FIELD OF THE INVENTION

The present invention relates to pharmaceutical compositions comprising a therapeutically effective amount of vitamin A palmitate; processes for their preparation; and uses and methods of treatment comprising them.

The compositions provided by the present invention may be used in the treatment and/or prophylaxis of conditions and diseases caused by vitamin A deficiency.

BACKGROUND OF THE INVENTION

Vitamin A deficiency can result from inadequate intake, fat malabsorption, or liver disorders. In premature births, early separation from normal umbilical nutrition also results in critical deficits in a wide range of nutrients and metabolites including vitamin A. Deficiency impairs immunity and hematopoiesis and causes rashes and induced ocular irregularities, for example, xerophthalmia and night blindness. Treatment consists of vitamin A given orally or, if symptoms are severe or malabsorption is the cause, parenterally.

Primary vitamin A deficiency is usually caused by prolonged dietary deprivation. It is endemic in areas such as southern and eastern Asia, where rice, devoid of beta-carotene, is the staple food. Secondary vitamin A deficiency may be due to decreased bioavailability of provitamin A carotenoids, or interference with absorption, storage or transport of vitamin A. Interference with absorption or storage is likely in celiac disease, cystic fibrosis, pancreatic insufficiency, duodenal bypass, chronic diarrhea, bile duct obstruction, giardiasis, and cirrhosis.

Impaired dark adaptation of the eyes, which can lead to night blindness, is an early symptom of vitamin A deficiency. Xerophthalmia (which is nearly pathognomonic) results from keratinization of the eyes. It involves drying (xerosis) and thickening of the conjunctivae and corneas. Superficial foamy patches composed of epithelial debris and secretions on the exposed bulbar conjunctiva (Bitot spots) develop. In advanced deficiency, the cornea becomes hazy and can develop erosions, which can lead to its destruction (keratomalacia).

The younger the patient, the more severe are the effects of vitamin A deficiency. Growth retardation and infections are common among children. Mortality rate can exceed 50% in children with severe vitamin A deficiency.

Other conditions associated with vitamin A deficiency include neonatal sepsis, hospital-acquired sepsis, sepsis from premature rupture of membranes, measles, meningitis, pneumonia, necrotizing enterocolitis, and other viral or bacterial infections.

Despite technological advances, premature births and their associated complications continue to be a major public health care problem. Each year, 10,000 to 15,000 infants develop chronic lung disease (CLD) of prematurity, also called bronchopulmonary dysplasia (BPD), (see, for example, Bronchopulmonary Dysplasia, National Heart, Lung and Blood Institute (NHLBI) [Internet] https://www, nhlbi.nih.gov/health-topics/bronchopulmonary-dylplasia, and Strueby, L., Thebaud, B., Advances in bronchopulmonary dysplasia, Expert Rev Respir Med, 2014 Jun. 8 (3); 327-38). Many affected infants require prolonged mechanical ventilation or oxygen support, have recurrent hospitalizations for respiratory infections, and other problems such as persistent airway obstruction and delayed distal lung growth (see, for example, Baker, C. D., Alvira, C. M., Disrupted lung development and bronchopulmonary dysplasia: opportunities for lung repair and regeneration, Curr Opin Pediatr. 2014, Jun. 26 (3): 306-14). Contrary to the previous belief that due to the compensatory lung growth, with age, BPD would get corrected (see, for example, O'Reilly, M., Sozo, F., Harding, R., Impact of preterm birth and bronchopulmonary dysplasia on the developing lung: long-term consequences for respiratory health, Clin Exp Pharmacol Physiol., 2013, November 40(11), 765-73), evidence suggests that even mild BPD cases continue to show impaired lung function in childhood and beyond (see, for example, Grenough, A., et al., Lung volumes in infants who had mild to moderate bronchopulmonary dysplasia, Eur J Pediatr, 2005 September 164 (9) 583-6). In fact, impaired lung function in infants with BPD persists into adulthood, contributing to adult chronic respiratory diseases with concern that those individuals who had BPD as babies never achieve normal lung function (see, for example, Bronchopulmonary Dysplasia, National Heart, Lung and Blood Institute (NHLBI) [Internet] https://www.nhlbi.nih.gov/health-topics/bronchopulmonary-dylplasia, and Wong P M, Lees A N, Louw J, et al. Emphysema in young adult survivors of moderate-to-severe bronchopulmonary dysplasia. Eur Respir J 2008; 32(2):321-8). Moreover, infants with BPD also have impaired physical growth, neurocognitive delays and cardiac dysfunction including pulmonary hypertension (see, for example, Cerny L, Torday J S, Rehan V K. Prevention and treatment of bronchopulmonary dysplasia: contemporary status and future outlook. Lung 2008; 186(2): 75-89, and Levy P T, Dioneda B, Holland M R, et al. Right ventricular function in preterm and term neonates: reference values for right ventricle areas and fractional area of change. J Am Soc Echocardiogr 2015; 28(5):559-69). Despite all recent progress in understanding the pathophysiology of BPD, other than vitamin A administration, there is no therapeutic option that has been consistently shown to be effective in clinical trials and on meta-analyses. However, vitamin A therapy in its present form has not received extensive clinical acceptance.

For example, a currently approved formulation for parenteral administration of vitamin A contains chlorobutanol as a preservative (see, for example, AQUASOL A™, prescribing information). It has been suggested that chlorobutanol should not be used as a preservative in injectable preparations intended for neonates and children (see, for example, Pharmacy in Practice, May 2004, p. 101). Chlorobutanol has been implicated in producing somnolence in patients given high doses of salicylamide or morphine infusions with chlorobutanol as a preservative (see, for example, Borody, T. et al., Chlorbutanol toxicity and dependence, *Med J Aust* 1979; 1: 288; and DeChristoforo, R., et al., High-dose morphine infusion complicated by chlorobutanol-induced somnolence, *Annals of Internal Medicine* 1983; 98; 335-6). A delayed cellular type of hypersensitivity reaction to chlorobutanol used to preserve heparin when it was given by subcutaneous injection, has also been reported (see, for example, Dux, S., et al., Hypersensitivity reaction to chlorbutanol-preserved heparin, Lancet 1981; 1: 149).

Accordingly, refining vitamin A therapy for widespread clinical use would be a major step in preventing BPD, with clinical, financial and societal implications.

In preterm infants, vitamin A plays an important role in lung maturation and development. Vitamin A deficiency (VAD) has been implicated in the development of BPD in this fragile population, particularly given that the human fetus accumulates vitamin A primarily in the third trimester of pregnancy. The transport mechanism of vitamin A across the placenta, its regulation, and fetal stores have been the subjects of research over the past four decades. Premature infants have reduced hepatic stores of retinyl ester (see, for example, Mactier H, Weaver L T. Vitamin A and preterm infants: what we know, what we don't know, and what we need to know. Archives of Disease in Childhood—Fetal and Neonatal Edition 2005; 90(2):F103-8). In plasma, vitamin A is bound to a specific carrier protein, retinol-binding protein (RBP), and the resulting complex is further complexed with transthyretin (see, for example, Mactier H, Weaver L T. Vitamin A and preterm infants: what we know, what we don't know, and what we need to know. Archives of Disease in Childhood—Fetal and Neonatal Edition 2005; 90(2): F103-8). Premature infants have lower concentrations of plasma RBP than term infants, and most preterm infants have both low plasma vitamin A concentrations and low plasma retinol/RBP molar ratios, indicating that they are vitamin A deficient (see, for example, Shenai J P, Rush M G, Stahlman M T, Chytil F. Plasma retinol-binding protein response to vitamin A administration in infants susceptible to bronchopulmonary dysplasia. J Pediatr 1990; 116(4):607-14). Preterm infants with vitamin A concentrations below 200 μg/L (0.70 μmol/L) have been considered deficient, and concentrations below 100 μg/L are indicative of severe deficiency, and depleted liver stores (see, for example, Greene H L, Phillips B L, Franck L, et al. Persistently low blood retinol levels during and after parenteral feeding of very low birth weight infants: examination of losses into intravenous administration sets and a method of prevention by addition to a lipid emulsion. Pediatrics 1987; 79(6):894-900, and Shenai J P, Rush M G, Stahlman M T, Chytil F. Plasma retinol-binding protein response to vitamin A administration in infants susceptible to bronchopulmonary dysplasia. J Pediatr 1990; 116(4):607-14). Both the plasma RBP response and the relative rise in plasma retinol concentration following intramuscular (IM) vitamin A administration have been described as useful tests to assess functional vitamin A status (Zachman R D, Samuels D P, Brand J M, Winston J F, Pi J T. Use of the intramuscular relative-dose-response test to predict bronchopulmonary dysplasia in premature infants. Am J Clin Nutr 1996; 63(1):123-9).

Vitamin A has been shown to play a critical role in lung development, and VAD has been posited to predispose or contribute to BPD/CLD in these low birth-weight infants (see, for example, Chytil F. The lungs and vitamin A. Am J Physiol 1992; 262(5 Pt 1):L517-527; Shenai J P, Chytil F, Parker R A, Stahlman M T. Vitamin A status and airway infection in mechanically ventilated very-low-birth-weight neonates. Pediatr Pulmonol 1995; 19(5):256-61; Hustead V A, Gutcher G R, Anderson S A, Zachman R D. Relationship of vitamin A (retinol) status to lung disease in the preterm infant. J Pediatr 1984; 105(4):610-5; and Shenai J P, Chytil F, Stahlman M T. Vitamin A status of neonates with bronchopulmonary dysplasia. Pediatr Res 1985; 19(2):185-8). Indeed, two earlier studies reported that very low birth-weight infants who developed CLD had lower concentrations of vitamin A than similar infants without CLD (see, for example, Hustead V A, Gutcher G R, Anderson S A, Zachman R D. Relationship of vitamin A (retinol) status to lung disease in the preterm infant. J Pediatr 1984; 105(4): 610-5; and Shenai J P, Chytil F, Stahlman M T. Vitamin A status of neonates with bronchopulmonary dysplasia. Pediatr Res 1985; 19(2):185-8). Preclinical studies further support the contribution of low plasma and tissue concentrations of vitamin A to the development of BPD/CLD in preterm infants. VAD in laboratory animals has been shown to produce a sequence of histopathological changes in the respiratory tract epithelium including necrotizing tracheo-brochiolits and squamous metaplasia (see, for example, Lancillotti F, Darwiche N, Celli G, De Luca L M. Retinoid status and the control of keratin expression and adhesion during the histogenesis of squamous metaplasia of tracheal epithelium. Cancer Res 1992; 52(22):6144-52 and Baybutt R C, Hu L, Molteni A. Vitamin A deficiency injures lung and liver parenchyma and impairs function of rat type II pneumocytes. J Nutr 2000; 130(5):1159-65), which can be reversed by restoration of adequate vitamin A status (see, for example, Hind M, Maden M. Retinoic acid induces alveolar regeneration in the adult mouse lung. Eur Respir J 2004; 23(1):20-7). Similar changes are observed in ventilated infants with chronic neonatal lung injury, and who are vitamin A deficient (see, for example, Hustead V A, Gutcher G R, Anderson S A, Zachman R D. Relationship of vitamin A (retinol) status to lung disease in the preterm infant. J Pediatr 1984; 105(4):610-5).

Vitamin A supplementation facilitates healing and recovery from lung injury, and has been shown to reduce the incidence of BPD/CLD in preterm infants (see, for example, Guimaraes H, Guedes M B, Rocha G, Tome T, Albino-Teixeira A. Vitamin A in prevention of bronchopulmonary dysplasia. Curr Pharm Des 2012; 18(21):3101-13; Tropea K, Christou H. Current pharmacologic approaches for prevention and treatment of bronchopulmonary dysplasia. Int J Pediatr 2012; 2012:598606; and Young T E. Nutritional support and bronchopulmonary dysplasia. Journal of Perinatology 2007; 27:S75-8). Thus, there is compelling evidence to support that vitamin A supplementation can both prevent BPD/CLD, and treat the underlying progressive disease processes that begin within hours to days after birth. These underlying processes lead to the clinical manifestions that result in the diagnosis of BPD, defined either historically or per the current NIH definition of BPD (a need for supplemental oxygen at 36 weeks post menstrual age (PMA Ehrenkranz R A, Walsh M C, Vohr B R, et al. Validation of the National Institutes of Health Consensus Definition of Bronchopulmonary Dysplasia. Pediatrics 2005; 116(6): 1353-60), the latter including a severity sub-classification based on varying needs for supplemental oxygen or ventilatory support).

Oral dosing of vitamin A has been proven to be insufficient, because preterm neonates, especially very low birth-weight infants, are initially largely intolerant to enteral feeds, and absorption of vitamin A by the immature gut is generally poor (see, for example, Rush M G, Shenal J P, Parker R A, Chytil F. Intramuscular versus enteral vitamin A supplementation in very low birth weight neonates. The Journal of Pediatrics 1994; 125(3):458-62). For preterm infants who are unable to tolerate oral feeds, typically total parenteral nutrition (TPN) is needed to provide nutrition. Despite addition of multivitamin preparations containing retinol (or equivalent) to the TPN, significant losses in delivered vitamin A occur, hypothesized as due to vitamin A photodegradation and/or from adsorption onto the intravenous tubing.

Intramuscular vitamin A monotherapy has been extensively evaluated, not only as a supplement in VAD in preterm infants, with a series of studies particularly highlighting vitamin A dosing for prevention and treatment of BPD/CLD (see, for example, Tyson J E, Wright L L, Oh W, et al. Vitamin A Supplementation for Extremely-Low-Birth-Weight Infants. New England Journal of Medicine 1999; 340(25):1962-8; Darlow B A, Graham P J, Rojas-Reyes M X. Vitamin A supplementation to prevent mortality and short- and long-term morbidity in very low birth weight infants. In: Cochrane Database of Systematic Reviews. John Wiley & Sons, Ltd; 2016. Available from: http://onlinelibrary.wiley.com/doi/10.1002/14651858.CD000501.pub4/abstract; Kennedy K A, Cotten C M, Watterberg K L, Carlo W A. Prevention and management of bronchopulmonary dysplasia: Lessons learned from the neonatal research network. Seminars in Perinatology 2016; 40(6):348-55; and Couroucli X I, Placencia J L, Cates L A, Suresh G K. Should we still use vitamin A to prevent bronchopulmonary dysplasia? J Perinatol 2016; 36(8):581-5).

SUMMARY OF THE INVENTION

The present invention provides a pharmaceutical composition comprising vitamin A palmitate, a surfactant and water and, preferably, which is suitable for oral and/or parenteral administration. The invention also provides for pharmaceutical compositions prepared by processes according to the present invention, along with such processes.

The invention further provides for methods of treatment comprising administration of these pharmaceutical compositions, and for uses of these pharmaceutical compositions.

DETAILED DESCRIPTION OF THE INVENTION

Vitamin A palmitate is the palmitate ester of retinol. Retinol has the following structure:

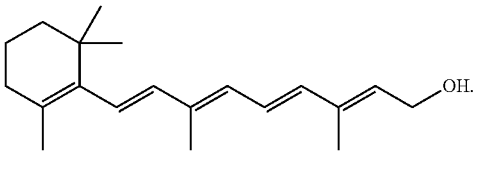 [SMILES: CC1=C(/C=C/C(C)=C/C=C/C(C)=C/CO)C(C)(C)CCC1]

It should be noted that this structure depicts the "all trans" form of retinol, which is the usual form of vitamin A used therapeutically. A variety of other forms exist that contain one or more cis bonds or other alterations to the all trans bond configuration, including, for example, 13-cis-retinol (also known as isotretinoin), 9-cis-retinol, 9,13-dicis-retinol and 3,4-didehydroretinol.

Surfactants for use according to the present invention include, but are not limited to, polysorbate 20 (for example Tween® 20, polysorbate 60 (for example Tween® 60), polysorbate 80 (for example Tween® 80), stearyl alcohol, a polyethylene glycol derivative of hydrogenated castor oil (for example Cremophor® RH 40), a polyethylene glycol derivative of hydrogenated castor oil for example Cremophor® RH 60), sorbitan monolaurate (for example Span® 20), sorbitan monopalmitate (for example Span® 40), sorbitan monostearate (for example Span® 60), polyoxyethylene (20) oleyl ether (for example Brij® 020), polyoxyethylene (20) cetyl ether (for example Brij® 58), polyoxyethylene (10) cetyl ether (for example Brij® C10), polyoxyethylene (10) oleyl ether (for example Brij® 010), polyoxyethylene (100) stearyl ether (for example Brij® S100), polyoxyethylene (10) stearyl ether (for example Brij® S10), polyoxyethylene (20) stearyl ether (for example Brij® S20), polyoxyethylene (4) lauryl ether (for example Brij® L4), polyoxyethylene (20) cetyl ether (for example Brij® 93), polyoxyethylene (2) cetyl ether (for example Brij® S2), caprylocaproyl polyoxyl-8 glyceride (for example) Labrasol®, polyethylene glycol (20) stearate (for example Myrj™ 49), polyethylene glycol (40) stearate (for example Myrj™ S40), polyethylene glycol (100) stearate (for example Myrj™ S100), polyethylene glycol (8) stearate (for example Myrj™ S8), and polyoxyl 40 stearate (for example Myrj™ 52), and mixtures thereof.

In an embodiment of the present invention, the surfactant is polysorbate 80.

Polysorbate 80 (polyoxyethylene (20) sorbitan monooleate), has the following general structure:

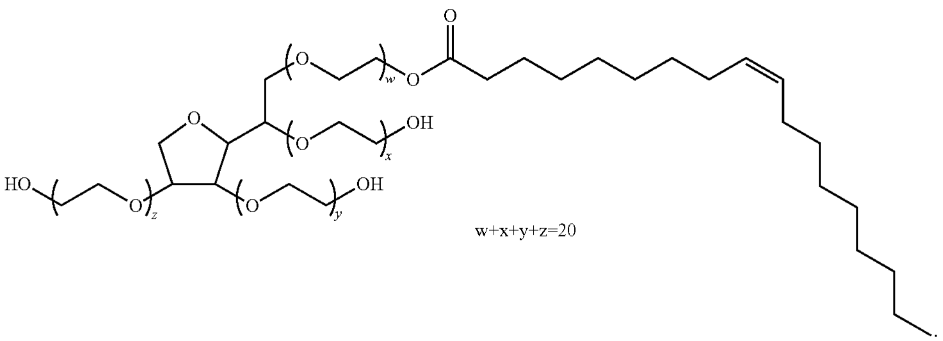

w+x+y+z=20

With regard to the fatty acid content of polysorbate 80, the United States Pharmacopeia, and other national formularies, indicate that the acceptable criteria for the fatty acid oleic acid content is 58% or greater. Other fatty acids may be present, for example, myristic acid with acceptance criteria of up to 5.0%, palmitic acid up to 16.0%, stearic acid up to 6.0%, linoleic acid up to 18.0%, and linolenic acid up to 4.0%.

Polysorbate 80 at the USP acceptable level of purity may be used in the compositions of the present invention, as may be formulations of polysorbate 80 at higher levels of purity, for example between 85% and 100% oleic acid (for example, Super-Refined™ Polysorbate available from Croda), and greater than 98% oleic acid (for example, Polysorbate 80 (HX2)™ available from NOF).

Phase Inversion

Phase inversion refers to a phenomenon that occurs when enough water or an aqueous medium is added to a primarily oily mixture and, upon agitation, transitions to being an oil-in-water emulsion, or similarly, when oil is added to a primarily aqueous solution resulting in a water-in-oil emulsion. The phase inversion process can lead to the formation of finely dispersed droplets in a continuous phase. The process is strongly affected by the preparation method, and very different droplet size distribution can occur. Droplet size is also linked to product stability. There is a variety of phenomena acting to influence the morphology of the system, and eventually leading to undesirable phase separation including coalescence (two droplets merge into one), collision, creaming and sedimentation, and flow induced droplet rearranging. It is known, for example, that oil-in-water emulsions are unstable due to the creaming that becomes significant when the droplet radius is greater than 0.5 μm (See, for example, Preziosi, V., et al., *Chemical Engineering Transactions*; Vol. 32, 2013, pp.1585-1590). The main mechanism responsible for an increase in droplet size is coalescence, which can be inhibited by using surfactants. Phase inversion, i.e. the phenomenon by which the dispersed phase becomes the continuous (dominant) phase and vice-versa, is a useful route to produce emulsions made up of very fine droplets. This can be brought about, for example, by changing the temperature of the system, changing the volume fraction of the phases, imposing particular conditions of agitation, and particular mixing conditions.

The compositions of the present invention, and the processes by which they are prepared, are the result of the unexpected bringing together of conditions of preparation which facilitate the formation of stable compositions having properties desirable for pharmaceutical use.

Micelles

By 'micelle' is meant an assembly of molecules, generally of the class known as detergents or similar amphipathic molecules having both hydrophobic and hydrophilic characteristics, which form into a sphere or other compact shapes with the outer surface being comprised by a monolayer of the detergent molecules, which in aqueous solutions form with the hydrophilic portions facing outward and the hydrophobic portions facing inward. The hydrophilic portions of the detergent interact with water, facilitating a situation in which the micelles are stably dispersed or dissolved in aqueous media. The hydrophobic core of micelles is useful for interacting with other hydrophobic molecules, providing a hydrophobic environment within which these other hydrophobic molecules, as in the case with the water-insoluble vitamin A palmitate, can be fat-dissolved inside the micelles, and because of the hydrophilic surface of the micelles, these otherwise water-insoluble hydrophobic molecules are facilitated to be miscible within aqueous solutions.

Micelles are typically small, and when they are generally of similar density as water, they can remain dissolved indefinitely. Such permanent miscibility is a preferred feature of the pharmaceutical compositions of the present invention.

Micelle size may be determined by methods known in the art. Visual inspection can be used, in the first instance, to determine visual clarity. Quantitation of light scattering, for example at 400 nm, and by dynamic light scattering (DLS) may be used to directly assess micelle radii and size distribution.

Definitions

By "pharmaceutically acceptable acid" is meant acids which are not biologically or otherwise undesirable in pharmaceutical compositions of the present invention. Pharmaceutically acceptable acids can be inorganic acids, for example hydrochloric acid, hydrobromic acid, sulfuric acid, nitric acid, phosphoric acid and the like, or organic acids, for example acetic acid, oleic acid, palmitic acid, stearic acid, glycolic acid, pyruvic acid, oxalic acid, maleic acid, malonic acid, succinic acid, fumaric acid, tartaric acid, citric acid, ascorbic acid, lactic acid, tartaric acid and the like.

By "pharmaceutically acceptable base" is meant bases which are not biologically or otherwise undesirable in pharmaceutical compositions of the present invention. Pharmaceutically acceptable bases include sodium hydroxide, ammonium hydroxide, potassium hydroxide, histidine, arginine and lysine.

By "therapeutically effective amount", "therapeutically effective dose", or "pharmaceutically effective amount" is meant an amount of vitamin A palmitate, as disclosed for this invention, which has a therapeutic effect, that is an amount that relieves to some extent, or prevents one or more symptoms of vitamin A deficiency. The doses of vitamin A palmitate which are useful in treatment are therapeutically effective amounts. Thus, as used herein, a therapeutically effective amount means those amounts of vitamin A palmitate which produce the desired therapeutic effect as judged by clinical trial results and/or model animal studies, or which has been proven to be effective in routine medical practice to benefit a patient.

By "parenteral administration" is meant routes of administration known to those skilled in the art, and include subcutaneous administration, intraperitoneal administration, intravenous administration, intradermal administration and intramuscular administration.

By "suitable for parenteral administration" is meant that the pharmaceutical composition of the present invention meets quality standards known to those skilled in the art as found, for example, in the United States Pharmacopeia, the European Pharmacopeia, and the Japanese Pharmacopeia. Such standards include, for example that the composition by sterile and pyrogen-free, that it be clear, or practically exempt of visible particles, and also free of sub-visible particles as required by these pharmacopeias, and that there is no evidence of phase separation or aggregate formation.

The amount of the vitamin A palmitate and daily dose can be routinely determined by one of skill in the art, and will vary, depending on several factors, such as the patient's height, weight, sex, age and medical history. For prophylactic treatments, a therapeutically effective amount is that amount which would be effective to prevent a condition caused by vitamin A deficiency.

"Treat", "treatment", or "treating" as used herein refers to administering a pharmaceutical composition for prophylactic and/or therapeutic purposes.

The term "prophylactic treatment" or "prophylaxis" refers to treating a patient who does not have symptoms of a condition or conditions caused by vitamin A deficiency, but who is susceptible to, or otherwise at risk of such condition or conditions. The term "therapeutic treatment" refers to administering treatment to a patient already suffering from a condition or conditions caused by vitamin A deficiency. Thus, in preferred embodiments, treating is the administration to a mammal (either for therapeutic or prophylactic purposes) of a prophylactically and/or therapeutically effective amounts of vitamin A palmitate.

By "homogeneous intermediate state" is meant a mixture at or near the water-in-oil, oil-in-water inversion point.

The term "substantially all" refers to an amount of 95% or greater. The term "patient" as used herein refers to a mammal, preferably a human.

Pharmaceutical Compositions

Preparation of the compositions of the present invention occurs generally, in a two-step process. The first is a slow, controlled introduction of water, or warm water, to a warmed premixture of vitamin A palmitate and a surfactant, or a mixture of surfactants. The second is a final addition of water at lower temperatures followed by measurement of pH and adjustment of the pH if necessary. Sterilization by filtration is then done, followed by appropriate packaging.

To begin, the target, full volume of water is dispensed into a vessel, followed by bubbling nitrogen through the water to purge dissolved oxygen. It should be noted that vitamin A palmitate is sensitive to both oxygen and light. Operations are carried out under an inert, oxygen free, atmosphere, and under light restricting conditions. Vitamin A palmitate is pre-warmed, and the necessary amount is measured out and added into a vessel containing the required amount of surfactant, or a mixture of surfactants. This is agitated gently, to avoid formation of bubbles within the mixture, and a portion of the final amount of water is added slowly to the mixture. After stirring for an appropriate time, the material reaches an oil-in-water, water-in-oil inversion point, sometimes also referred to as a liquid crystal state.

The vessel is cooled, and the remaining water (except for approximately 5% or less of the remaining water which may be reserved for forming a solution or solutions of an appropriate acid and/or base) is added as a single bolus, and stirring continued, to form a clear, amber-colored liquid. At this point the pH is adjusted, if desired, by addition of an appropriate acid or base, or a solution or solutions of an appropriate acid or base. A typical pharmaceutical product target pH is between pH 7.0 and 7.5.

The material may then be sterile-filtered, for example, through a 0.22 micron or 0.10 micron filter. Such filters include nitrocellulose, or other material membranes in which the pore size can be reproducibly controlled and which are generally inert so the membrane material does not alter the chemical content of the filtrate.

It should be noted that packaging, for example vials for parenteral injection, should be prepared such that the head space above the composition of the present invention should be primarily nitrogen, or other oxygen-depleted gas.

Use in Treatment and/or Prophylaxis

The pharmaceutical compositions according to the present invention are intended for the use in the treatment and/or prophylaxis of vitamin A deficiency disorders. Such deficiency disorders include, but are not limited to, bronchopulmonary dysplasia and retinopathy of prematurity, neonatal sepsis, hospital acquired sepsis, sepsis from premature rupture of membranes, measles, meningitis, pneumonia, necrotizing enterocolitis, and other viral or bacterial infections.

Dosing of Vitamin A Palmitate

The amount of vitamin A palmitate, the frequency of administration, and length of time for a given course of treatment can be routinely determined by one of skill in the art, and will vary, depending on several factors, which may include the patient's height, weight, sex, age, and medical history. For prophylactic treatments, the dosing and regimen would be those which prevent the development of a vitamin A deficiency disorder.

The amount of vitamin A palmitate may be expressed USP units, international units, or as a weight of vitamin A palmitate. One USP unit is equivalent to one international unit, and is equivalent to 0.3 mcg of retinol.

Examples of dosing include intramuscular injection of 100,000 Units daily for three days, followed by 50,000 units daily for two weeks for adults; 17,500 to 35,000 Units daily for 10 days for pediatric patients 1 to 8 years old; and 7,500 to 15,000 units daily for ten days for infants. For prevention of BPD in premature neonates, a typical course is 5,000 units by intramuscular injection, 3 times per week, for 4 weeks.

Accordingly, in one embodiment of the present invention, a pharmaceutical composition is provided, comprising between 0.03% (w/w) and 4.0% (w/w) vitamin A palmitate, a weight of a surfactant which is 4.0 times or more of the weight of the vitamin A palmitate contained in the composition, wherein the remainder of the composition comprises water, and, optionally, wherein the pH has been adjusted to between pH 7.0 and pH 7.5 by addition of a pharmaceutically acceptable acid and/or a pharmaceutically acceptable base, and wherein the composition is composed of particles having outward faces, comprised of the hydrophilic portion of the surfactant molecules, that interact with water and inner portions that are hydrophobic, being comprised of the hydrophobic portion of the surfactant molecules and substantially all of the vitamin A palmitate introduced into the composition.

In another embodiment of the present invention, a pharmaceutical composition is provided comprising between 0.03% (w/w) and 4.0% (w/w) vitamin A palmitate, a weight of a surfactant which is between 4.0 times and 5.0 times the weight of the vitamin A palmitate contained in the composition, wherein the remainder of the composition comprises water, and, optionally, wherein the pH has been adjusted to a pharmaceutically appropriate pH by addition of a pharmaceutically acceptable acid and/or a pharmaceutically acceptable base, and wherein the composition is composed of particles having outward faces, comprised of the hydrophilic portion of the surfactant molecules, that interact with water and inner portions that are hydrophobic, being comprised of the hydrophobic portion of the surfactant molecules and substantially all of the vitamin A palmitate introduced into the composition. In a further embodiment, the surfactant is selected from polysorbate 20, polysorbate 60, polysorbate 80, stearyl alcohol, a polyethylene glycol derivative of hydrogenated castor oil, a polyethylene glycol derivative of hydrogenated castor oil, sorbitan monolaurate, sorbitan monopalmitate, sorbitan monostearate, polyoxyethylene (20) oleyl ether, polyoxyethylene (20) cetyl ether, polyoxyethylene (10) cetyl ether, polyoxyethylene (10) oleyl ether, polyoxyethylene (100) stearyl ether, polyoxyethylene (10) stearyl ether, polyoxyethylene (20) stearyl ether, polyoxyethylene (4) lauryl ether, polyoxyethylene (20) cetyl ether, polyoxyethylene (2) cetyl ether, caprylocaproyl polyoxyl-8 glyceride, polyethylene glycol (20) stearate, polyethylene glycol (40) stearate, polyethylene glycol, polyethylene glycol (8) stearate, and polyoxyl 40 stearate, and mixtures thereof.

In another embodiment of the present invention a pharmaceutical composition is provided comprising between 0.03% (w/w) and 4.0% (w/w) vitamin A palmitate, a weight of polysorbate 80 which is between 4.0 times and 5.0 times the weight of the vitamin A palmitate contained in the composition, wherein the remainder of the composition comprises water, and, optionally, wherein the pH has been adjusted to a pharmaceutically appropriate pH by addition of a pharmaceutically acceptable acid and/or a pharmaceutically acceptable base, and wherein the composition is composed of particles having outward faces, comprised of the hydrophilic portion of the polysorbate 80 molecules, that interact with water and inner portions that are hydrophobic, being comprised of the hydrophobic portion of the polysorbate 80 molecules and substantially all of the vitamin A palmitate introduced into the composition. In another embodiment of the present invention, the pharmaceutically appropriate pH is between 7.0 and 7.5. In a further embodiment the particles formed by vitamin A palmitate and polysorbate 80 are in the configuration of micelles having a diameter of less than or equal to 500 nm. In a further embodiment, the micelles have a diameter of less than or equal to 250 nm. In a further embodiment, the micelles have a diameter of less than or equal to 100 nm. In another embodiment a pharmaceutical composition is provided comprising between 0.3% and 3.0% vitamin A palmitate. In a further embodiment a pharmaceutical composition is provided comprising between 2.5% and 3.0% vitamin A palmitate. In another embodiment, the fatty acid content of the polysorbate 80 is between 58% and 100% oleic acid. In a further embodiment, the fatty acid content of the polysorbate 80 is between 85% and 100% oleic acid. In a further embodiment of the present invention, the fatty acid content of the polysorbate 80 is greater than or equal to 98% oleic acid. In another embodiment of the present invention the pharmaceutically acceptable acid is selected from hydrochloric acid, hydrobromic acid, sulfuric acid, nitric acid, phosphoric acid, acetic acid, oleic acid, palmitic acid, stearic acid, glycolic acid, pyruvic acid, oxalic acid, maleic acid, malonic acid, succinic acid, fumaric acid, tartaric acid, citric acid, ascorbic acid, lactic acid, and tartaric acid. In a further embodiment, the pharmaceutically acceptable base is selected from sodium hydroxide, ammonium hydroxide, potassium hydroxide, histidine, arginine and lysine. In a further embodiment the pharmaceutically acceptable acid is citric acid, and the pharmaceutically acceptable base is sodium hydroxide. In a further embodiment of the present invention a pharmaceutical composition is provided wherein the composition is suitable for parenteral administration. In another embodiment of the present invention, a method of treatment or prophylaxis of a vitamin A disorder, in a patient in need thereof, is provided comprising administration of a pharmaceutically effective amount of a pharmaceutical composition according to the present invention. In a further embodiment, the vitamin A disorder is selected from neonatal sepsis, hospital-acquired sepsis, sepsis from premature rupture of membranes, bronchopulmonary dysplasia, retinopathy of prematurity, measles, meningitis, pneumonia, necrotizing enterocolitis, a viral infection and a bacterial infection, and a combination of such disorders. In a further embodiment a method of treatment or prophylaxis of a vitamin A deficiency disorder, in a patient in need thereof, comprising oral or parenteral administration of a pharmaceutically effective amount of a pharmaceutical composition suitable for oral or parenteral administration according to the present invention. In a further embodiment, the patient is a human born prematurely, or a neonate. In a further embodiment, the vitamin A deficiency disorder is bronchopulmonary dysplasia or retinopathy of prematurity. In a further embodiment, the vitamin A deficiency disorder is bronchopulmonary dysplasia. In a further embodiment of the present invention, the pharmaceutical composition of the present invention is for use in the treatment or prophylaxis of a vitamin A deficiency disorder in a patient in need thereof. In a further embodiment, the vitamin A disorder is selected from neonatal sepsis, hospital-acquired sepsis, sepsis from premature rupture of membranes, bronchopulmonary dysplasia, retinopathy of prematurity, measles, meningitis, pneumonia, necrotizing enterocolitis, a viral infection and a bacterial infection, and a combination of such disorders. In a further embodiment, a pharmaceutical composition is provided for use in the treatment or prophylaxis of a vitamin A deficiency disorder wherein the patient is a human born prematurely or a neonate. In a further embodiment a pharmaceutical composition is provided for use in the treatment or prophylaxis of bronchopulmonary dysplasia or retinopathy of prematurity. In a further embodiment a pharmaceutical composition is provided for use in the treatment or prophylaxis of bronchopulmonary dysplasia.

In another embodiment of the present invention a pharmaceutical composition is provided which is prepared by a process comprising the following steps:

(1) preparation of a mixture by combining vitamin A palmitate, and 4 to 5 times the weight of vitamin A palmitate of a surfactant;
(2) warming the mixture resulting from step (1) to a temperature of between 40° C. and 70° C., and agitating until homogeneous;
(3) addition of water which has been warmed to a temperature of between 40° C. and 70° C. in an amount of between 20% and 80% of the weight of the mixture of step (1), with agitation, over a period of time of between 5 and 90 minutes to afford a homogeneous intermediate state;
(4) cooling of the mixture from step (3) to a temperature of between 15° C. and 40° C.;
(5) addition of water as a bolus in an amount, or about 95% or greater of this amount, to achieve the appropriate final concentration of vitamin A palmitate, followed by agitation for between 5 minutes and 6 hours to afford a stable mixture comprising the appropriate micelle size;
(6) adjustment of the pH of the mixture from step (5), if necessary, to a pharmaceutically acceptable pH by addition of a pharmaceutically acceptable acid and/or pharmaceutically acceptable base, or a solution or solutions of the acid and/or base, and/or addition of water, resulting in the final appropriate concentration of vitamin A palmitate; and
(7) sterilization of the mixture from step (6) by filtration through a filter having a pore size of between 0.1 micron and 0.22 micron.

In a further embodiment, the surfactant is selected from polysorbate 20, polysorbate 60, polysorbate 80, stearyl alcohol, a polyethylene glycol derivative of hydrogenated castor oil, a polyethylene glycol derivative of hydrogenated castor oil, sorbitan monolaurate, sorbitan monopalmitate, sorbitan monostearate, polyoxyethylene (20) oleyl ether, polyoxyethylene (20) cetyl ether, polyoxyethylene (10) cetyl ether, polyoxyethylene (10) oleyl ether, polyoxyethylene (100) stearyl ether, polyoxyethylene (10) stearyl ether, polyoxyethylene (20) stearyl ether, polyoxyethylene (4) lauryl ether, polyoxyethylene (20) cetyl ether, polyoxyethylene (2) cetyl ether, caprylocaproyl polyoxyl-8 glyceride, polyethylene glycol (20) stearate, polyethylene glycol (40) stearate, polyethylene glycol, polyethylene glycol (8) stearate, and polyoxyl 40 stearate, and mixtures thereof.

In another embodiment of the present invention a pharmaceutical composition is provided which is prepared by a process comprising the following steps:

(1) preparation of a mixture by combining vitamin A palmitate, and 4 to 5 times the weight of vitamin A palmitate of polysorbate 80;

(2) warming the mixture resulting from step (1) to a temperature of between 40° C. and 70° C., and agitating until homogeneous;

(3) addition of water which has been warmed to a temperature of between 40° C. and 70° C. in an amount of between 20% and 80% of the weight of the mixture of step (1), with agitation, over a period of time of between 5 and 90 minutes to afford a homogeneous intermediate state;

(4) cooling of the mixture from step (3) to a temperature of between 15° C. and 40° C.;

(5) addition of water as a bolus in an amount, or about 95% or greater of this amount, to achieve the appropriate final concentration of vitamin A palmitate, followed by agitation for between 5 minutes and 6 hours to afford a stable mixture comprising the appropriate micelle size;

(6) adjustment of the pH of the mixture from step (5), if necessary, to a pharmaceutically acceptable pH by addition of a pharmaceutically acceptable acid and/or pharmaceutically acceptable base, or a solution or solutions of the acid and/or base, and/or addition of water, resulting in the final appropriate concentration of vitamin A palmitate; and (7) sterilization of the mixture from step (6) by filtration through a filter having a pore size of between 0.1 micron and 0.22 micron.

In a further embodiment, the pharmaceutically acceptable pH is between pH 7.0 and pH 7.5. In a further embodiment, the mixture resulting from step (1) is warmed to a temperature of between 45° C. and 60° C. In a further embodiment the mixture resulting from step (1) is warmed to a temperature of between 50° C. and 60° C. In a further embodiment, the amount of water added in step (3) is between 35% and 70% of the weight of the mixture from step (1). In a further embodiment, the amount of water added in step (3) is between 50% and 60% of the weight of the mixture from step (1). In a further embodiment, the agitation of step (5) is carried out for a time between 30 minutes and 2 hours. In a further embodiment of the present invention, the cooling of step (4) is to a temperature of between 20° C. and 30° C. In a further embodiment, the pharmaceutically acceptable acid is selected from the pharmaceutically acceptable acid is selected from hydrochloric acid, hydrobromic acid, sulfuric acid, nitric acid, phosphoric acid, acetic acid, oleic acid, palmitic acid, stearic acid, glycolic acid, pyruvic acid, oxalic acid, maleic acid, malonic acid, succinic acid, fumaric acid, tartaric acid, citric acid, ascorbic acid, lactic acid, and tartaric acid. In a further embodiment, the pharmaceutically acceptable base is selected from sodium hydroxide, ammonium hydroxide, potassium hydroxide, histidine, arginine and lysine. In a further embodiment of the present invention, the pharmaceutically acceptable acid is citric acid, and the pharmaceutically acceptable base is sodium hydroxide. In a further embodiment, the pharmaceutical composition prepared by the above process embodiment is suitable for oral or parenteral administration. In a further embodiment, a method of treatment or prophylaxis of a vitamin A deficiency disorder, in a patient in need thereof, is provided comprising administration of a pharmaceutically effective amount of a pharmaceutical composition prepared the process of the present invention. In a further embodiment a method of treatment or prophylaxis of a vitamin A deficiency disorder, in a patient in need thereof, comprising parenteral administration of a pharmaceutically effective amount of a pharmaceutical composition prepared by the process of the present invention, which is suitable for parenteral or oral administration according to the present invention. In a further embodiment, the vitamin A disorder is selected from neonatal sepsis, hospital-acquired sepsis, sepsis from premature rupture of membranes, bronchopulmonary dysplasia, retinopathy of prematurity, measles, meningitis, pneumonia, necrotizing enterocolitis, a viral infection and a bacterial infection, and a combination of such disorders. In a further embodiment, the patient is a human born prematurely, or a neonate. In a further embodiment, the vitamin A deficiency disorder is bronchopulmonary dysplasia or retinopathy of prematurity. In a further embodiment, the vitamin A deficiency disorder is bronchopulmonary dysplasia. In a further embodiment of the present invention, the pharmaceutical composition of the present invention is for use in the treatment or prophylaxis of a vitamin A deficiency disorder in a patient in need thereof. In a further embodiment, the vitamin A disorder is selected from neonatal sepsis, hospital-acquired sepsis, sepsis from premature rupture of membranes, bronchopulmonary dysplasia, retinopathy of prematurity, measles, meningitis, pneumonia, necrotizing enterocolitis, a viral infection and a bacterial infection, and a combination of such disorders. In a further embodiment, a pharmaceutical composition prepared by the process of the present invention is provided for use in the treatment of a vitamin A deficiency disorder wherein the patient is a human born prematurely or a neonate. In a further embodiment a pharmaceutical composition prepared by the process of the present invention is provided for use in the treatment or prophylaxis of bronchopulmonary dysplasia or retinopathy of prematurity. In a further embodiment a pharmaceutical composition prepared by the process of the present invention is provided for use in the treatment or prophylaxis of bronchopulmonary dysplasia.

In another embodiment of the present invention a process for the preparation of the pharmaceutical compositions of the present invention is provided comprising the following steps:

(1) preparation of a mixture by combining vitamin A palmitate, and 4 to 5 times the weight of vitamin A palmitate of a surfactant;

(2) warming the mixture resulting from step (1) to a temperature of between 40° C. and 70° C., and agitating until homogeneous;

(3) addition of water which has been warmed to a temperature of between 40° C. and 70° C. in an amount of between 20% and 80% of the weight of the mixture of step (1), with agitation, over a period of time of between 5 and 90 minutes to afford a homogeneous intermediate state;

(4) cooling of the mixture from step (3) to a temperature of between 15° C. and 40° C.;

(5) addition of water as a bolus in an amount, or about 95% or greater of this amount, to achieve the appropriate final concentration of vitamin A palmitate, followed by agitation for between 5 minutes and 6 hours to afford a stable mixture comprising the appropriate micelle size;

(6) adjustment of the pH of the mixture from step (5), if necessary, to a pharmaceutically acceptable pH by addition of a pharmaceutically acceptable acid and/or pharmaceutically acceptable base, or a solution or solutions of the acid and/or base, and/or addition of water resulting in the final appropriate concentration of vitamin A palmitate; and (7) sterilization of the from step (6) by filtration through a filter having a pore size of between 0.1 micron and 0.22 micron.

In another embodiment, the surfactant is selected from polysorbate 20, polysorbate 60, polysorbate 80, stearyl alcohol, a polyethylene glycol derivative of hydrogenated castor oil, a polyethylene glycol derivative of hydrogenated castor oil, sorbitan monolaurate, sorbitan monopalmitate, sorbitan monostearate, polyoxyethylene (20) oleyl ether, polyoxyethylene (20) cetyl ether, polyoxyethylene (10) cetyl ether, polyoxyethylene (10) oleyl ether, polyoxyethylene (100) stearyl ether, polyoxyethylene (10) stearyl ether, polyoxyethylene (20) stearyl ether, polyoxyethylene (4) lauryl ether, polyoxyethylene (20) cetyl ether, polyoxyethylene (2) cetyl ether, caprylocaproyl polyoxyl-8 glyceride, polyethylene glycol (20) stearate, polyethylene glycol (40) stearate, polyethylene glycol, polyethylene glycol (8) stearate, and polyoxyl 40 stearate, and mixtures thereof.

In another embodiment of the present invention a process for the preparation of the pharmaceutical compositions of the present invention is provided comprising the following steps:

(1) preparation of a mixture by combining vitamin A palmitate, and 4 to 5 times the weight of vitamin A palmitate of polysorbate 80;

(2) warming the mixture resulting from step (1) to a temperature of between 40° C. and 70° C., and agitating until homogeneous;

(3) addition of water which has been warmed to a temperature of between 40° C. and 70° C. in an amount of between 20% and 80% of the weight of the mixture of step (1), with agitation, over a period of time of between 5 and 90 minutes to afford a homogeneous intermediate state;

(4) cooling of the mixture from step (3) to a temperature of between 15° C. and 40° C.;

(5) addition of water as a bolus in an amount, or about 95% or greater of this amount, to achieve the appropriate final concentration of vitamin A palmitate, followed by agitation for between 5 minutes and 6 hours to afford a stable mixture comprising the appropriate micelle size;

(6) adjustment of the pH of the mixture from step (5), if necessary, to a pharmaceutically acceptable pH by addition of a pharmaceutically acceptable acid and/or pharmaceutically acceptable base, or a solution or solutions of the acid and/or base, and/or addition of water resulting in the final appropriate concentration of vitamin A palmitate; and (7) sterilization of the from step (6) by filtration through a filter having a pore size of between 0.1 micron and 0.22 micron.

In a further embodiment, the pharmaceutically acceptable pH is between pH 7.0 and pH 7.5. In a further embodiment of the process according to the present invention, the mixture resulting from step (1) is warmed to a temperature of between 45° C. and 60° C. In a further embodiment, the mixture resulting from step (1) is warmed to a temperature of between 50° C. and 60° C. In a further embodiment, the amount of water added in step (3) is between 35% and 70% of the weight of the mixture from step (1). In a further embodiment, the amount of water added in step (3) is between 50% and 60% of the weight of the mixture from step (1). In a further embodiment, the agitation of step (5) is carried out for a time between 30 minutes and 2 hours. In a further embodiment, the cooling of step (4) is to a temperature of between 20° C. and 30° C. In a further embodiment, the pharmaceutically acceptable acid is selected from hydrochloric acid, hydrobromic acid, sulfuric acid, nitric acid, phosphoric acid, acetic acid, oleic acid, palmitic acid, stearic acid, glycolic acid, pyruvic acid, oxalic acid, maleic acid, malonic acid, succinic acid, fumaric acid, tartaric acid, citric acid, ascorbic acid, lactic acid, and tartaric acid. In a further embodiment, the pharmaceutically acceptable base is selected from sodium hydroxide, ammonium hydroxide, potassium hydroxide, histidine, arginine and lysine. In a further embodiment, the pharmaceutically acceptable acid of step (6) is citric acid, and the pharmaceutically acceptable base is sodium hydroxide.

EXAMPLES

The following examples serve to more fully describe the manner of using the above-described invention, as well as to set forth the best mode contemplated for carrying out various aspects of the invention. The Examples according to the invention are those falling within the scope of the claims herein.

Example 1

4.8 g of polysorbate 80 (PanReac AppliChem Tween® 80, USP-NF, pure, pharma grade) is dispensed into clean vessel. 1.1 g of vitamin A palmitate (DSM 1.7 MIU/g) that has been warmed to 48° C. is then added. This mixture is stirred in a water bath at 48° C. under an atmosphere of nitrogen for 5 minutes. 3.2 g of water is then added dropwise into the mixture over a period of 44 minutes, taking care that a homogeneous dispersion is accomplished before adding the next drop. This mixture is then stirred for 5 minutes to afford material which is at or near the water-in-oil, oil-in-water inversion point. The mixture is cooled to room temperature, and 31 g of water is added as a bolus. This mixture is then agitated for 1 hour, to afford a composition of the present invention, as a clear, amber-colored liquid.

Example 2

12.3 g of polysorbate 80 is dispensed into clean vessel. 2.8 g of vitamin A palmitate that has been warmed to 60° C. is then added. This mixture is stirred in a water bath at 60° C. under an atmosphere of nitrogen for 5 minutes. 8.0 g of water is then added dropwise into the mixture over a period of 9 minutes, taking care to allow each drop to disperse into the mixture before adding the next drop. This mixture is then stirred for 5 minutes to afford material which is at or near the water-in-oil, oil-in-water inversion point. The mixture is cooled to room temperature, and 31 g of water is added as a bolus. This mixture is then agitated for 50 minutes, to afford a composition of the present invention, as a clear, amber-colored liquid.

Example 3

23.9 g of polysorbate 80 (NOF Corporation HX2) is dispensed into a clean vessel. 5.47 g of prewarmed vitamin A palmitate is added and the mixture stirred for 5 minutes at a temperature of 57° C. A nitrogen blanket is used through this and the further procedures. 15.9 g of water is then added dropwise, over a period of 16 minutes. The mixture becomes viscous, and mild mechanical stirring is used, for an additional 5 minutes after this initial water addition. The mixture is cooled to 25° C., and 154 g of water, also at 25° C., is added as a single bolus. Stirring is maintained for 75 minutes to give a clear, amber-colored liquid. The pH is adjusted to pH 7.3 by addition of sodium hydroxide, to afford a composition of the present invention.

Example 4

23.9 g of polysorbate 80 (NOF Corporation HX2) is dispensed into a clean vessel. 5.47 g of prewarmed vitamin A palmitate is added and the mixture stirred for 5 minutes at a temperature of 57° C. A nitrogen blanket is used through this and the further procedures. 15.9 g of water is then added dropwise, over a period of 16 minutes, with stirring sufficient to ensure that each drop of water is thoroughly incorporated during dropwise introduction. The mixture is moved to a 25° C. environment, and 154 g of water, also at 25° C., is added as a single bolus. Stirring is maintained for at least 75 minutes, or until the formulation is uniformly dispersed resulting in a clear, amber-colored liquid. The pH is adjusted to pH 7.5 by addition of sodium hydroxide to afford a composition of the present invention.

What is claimed is:

1. A clear aqueous pharmaceutical composition comprising vitamin A palmitate and a surfactant, wherein:

95% or more of the vitamin A palmitate of the aqueous pharmaceutical composition comprises particles formed by the vitamin A palmitate and the surfactant in the configuration of micelles;

the vitamin A palmitate is present in the aqueous pharmaceutical composition at a concentration of 0.3% w/w to 3.0% w/w;

the weight of the surfactant present in the aqueous pharmaceutical composition is 4.0 to 5.0 times the weight of the vitamin A palmitate present in the aqueous pharmaceutical composition; and each of the micelles has a diameter of less than or equal to 500 nm.

2. The aqueous pharmaceutical composition according to claim 1, wherein the surfactant comprises polysorbate 20, polysorbate 60, polysorbate 80, stearyl alcohol, a polyethylene glycol derivative of hydrogenated castor oil, sorbitan monolaurate, sorbitan monopalmitate, sorbitan monostearate, polyoxyethylene (20) oleyl ether, polyoxyethylene (20) cetyl ether, polyoxymethylene (10) cetyl ether, polyoxyethylene (10) oleyl ether, polyoxyethylene (100) stearyl ether, polyoxyethylene (10) stearyl ether, polyoxyethylene (20) stearyl ether, polyoxyethylene (4) lauryl ether, polyoxyethylene (2) cetyl ether, caprylocaproyl polyoxyl-8 glyceride, polyethylene glycol (20) stearate, polyethylene glycol (40) stearate, polyethylene glycol, polyethylene glycol (8) stearate, or polyoxyl 40 stearate, or a mixture thereof.

3. The aqueous pharmaceutical composition according to claim 1, wherein the surfactant comprises polysorbate 80.

4. The aqueous pharmaceutical composition according to claim 1, wherein each micelle has a diameter of less than or equal to 250 nm.

5. The aqueous pharmaceutical composition according to claim 1, wherein each micelle has a diameter of less than or equal to 100 nm.

6. The aqueous pharmaceutical composition according to claim 1, wherein the vitamin A palmitate is present in the aqueous pharmaceutical composition at a concentration of 2.5% w/w to 3.0% w/w vitamin A palmitate.

7. The aqueous pharmaceutical composition according to claim 1, wherein:

the surfactant comprises polysorbate 80; and the fatty acid content of the polysorbate 80 is greater than or equal to 98% oleic acid.

8. The aqueous pharmaceutical composition according to claim 1, wherein:

the aqueous pharmaceutical composition comprises the conjugate base of citric acid; and the aqueous pharmaceutical composition comprises the conjugate acid of sodium hydroxide.

9. The aqueous pharmaceutical composition according to claim 1, wherein the aqueous pharmaceutical composition is configured for parenteral administration.

10. The aqueous pharmaceutical composition according to claim 1, wherein the aqueous pharmaceutical composition is configured for oral administration.

11. The aqueous pharmaceutical composition according to claim 1, wherein the aqueous pharmaceutical composition has a clarity of water.

12. The aqueous pharmaceutical composition according to claim 1, wherein the aqueous pharmaceutical composition has a clarity meeting or exceeding the standard set forth in the European Pharmacopeia 7.0.

13. The aqueous pharmaceutical composition according to claim 1, wherein the micelles are permanently miscible.

14. The aqueous pharmaceutical composition according to claim 1, wherein the aqueous pharmaceutical composition is configured for sterile filtration.

15. A method of treating a vitamin A deficiency disorder, comprising administering the aqueous pharmaceutical composition according to claim 1 to a subject in need thereof.

16. The method according to claim 15, wherein the vitamin A deficiency disorder comprises neonatal sepsis, hospital-acquired sepsis, sepsis from premature rupture of membranes, bronchopulmonary dysplasia, retinopathy of prematurity, measles, meningitis, pneumonia, necrotizing enterocolitis, a viral infection, or a bacterial infection, or a combination thereof.

* * * * *